(12) United States Patent
Hasegawa et al.

(10) Patent No.: US 7,481,115 B2
(45) Date of Patent: Jan. 27, 2009

(54) ULTRASONIC PROBE

(75) Inventors: Shigeyoshi Hasegawa, Tsukui-gun (JP); Kiyoshi Fujii, Yokohama (JP); Yukuo Sakagaito, Yokohama (JP)

(73) Assignee: Panasonic Corporation, Osaka (JP)

( * ) Notice: Subject to any disclaimer, the term of this patent is extended or adjusted under 35 U.S.C. 154(b) by 486 days.

(21) Appl. No.: 10/551,260

(22) PCT Filed: Mar. 29, 2004

(86) PCT No.: PCT/JP2004/004471
§ 371 (c)(1), (2), (4) Date: Sep. 27, 2005

(87) PCT Pub. No.: WO2004/086975
PCT Pub. Date: Oct. 14, 2004

(65) Prior Publication Data
US 2006/0191345 A1    Aug. 31, 2006

(30) Foreign Application Priority Data
Mar. 31, 2003   (JP)   ............... 2003-096244

(51) Int. Cl.
*G01N 29/24* (2006.01)
*A61B 8/12* (2006.01)
(52) U.S. Cl. ........................ 73/644; 600/462
(58) Field of Classification Search ........ None
See application file for complete search history.

(56) References Cited
U.S. PATENT DOCUMENTS
3,964,296 A * 6/1976 Matzuk ............ 73/607

4,375,818 A * 3/1983 Suwaki et al. ............... 600/463
5,313,950 A   5/1994 Ishikawa et al.
5,916,170 A * 6/1999 Kolz et al. .................. 600/462
6,296,610 B1 * 10/2001 Schneider et al. ........... 600/445
6,478,766 B1 * 11/2002 Chon .......................... 604/22
6,684,094 B1   1/2004 Lehr et al.
6,942,677 B2 * 9/2005 Nita et al. ................... 606/169

FOREIGN PATENT DOCUMENTS

| | | |
|---|---|---|
| EP | 0 089 131 | 9/1983 |
| JP | 62-167543 | 7/1987 |
| JP | 5-23342 | 2/1993 |
| JP | 8-112280 | 5/1996 |
| JP | 08112281 A * | 5/1996 |
| JP | 2001-327499 | 11/2001 |
| JP | 2001-327500 | 11/2001 |
| JP | 2002-301081 | 10/2002 |

* cited by examiner

*Primary Examiner*—Hezron Williams
*Assistant Examiner*—Rose M Miller
(74) *Attorney, Agent, or Firm*—Hamre, Schumann, Mueller & Larson, P.C.

(57) ABSTRACT

An ultrasonic probe according to the present invention includes: an ultrasonic element unit for transmitting and receiving an ultrasonic wave while carrying out ultrasonic scanning; a storage portion for storing the ultrasonic element unit; and an acoustic medium liquid charged in the storage portion. The ultrasonic element unit is supported by an elastic supporting member, and the storage portion is sealed by the supporting member in a liquid-tight state.

3 Claims, 4 Drawing Sheets

ULTRASONIC PROBE

TECHNICAL FIELD

The present invention relates to an ultrasonic probe, and more specifically to an ultrasonic probe with excellent resistance to an external shock.

BACKGROUND ART

A known ultrasonic probe for use in ultrasonic diagnostic apparatuses includes an ultrasonic element that is rotated in a storage portion filled with an acoustic coupling medium having an acoustic impedance similar to that of a living body, thereby transmitting and receiving ultrasonic waves. In such an ultrasonic probe, the ultrasonic element and a rotating mechanism portion for rotating the same are arranged in the storage portion, and these elements are fixed to a housing or a frame constituting the storage portion by fastening with screws, adhesive bonding with an adhesive, or the like (for example, JP 2001-327499 A).

However, when a great mechanical shock is applied externally to such a conventional ultrasonic probe due to, for example, dropping or damage caused by careless handling or the like, the shock is transmitted to the inside of the storage portion, so that the ultrasonic element and the rotating mechanism portion constituted by a precision mechanism are subjected to direct stress. In particular, an ultrasonic probe mainly intended for use in diagnosis of a body cavity is extremely small, and the shock applied to the precision mechanism therein results in a breakage or a failure of the probe.

Further, in a conventional ultrasonic probe, the storage portion usually is constituted by a window and a frame made of resin, the window and the frame being connected to each other. When an external shock is applied to this probe, a gap may be formed between the window and the frame, so that air bubbles enter the storage portion therethrough. Air bubbles in the storage portion act as a reflector of ultrasonic waves, and inhibit the transmission and reception of the ultrasonic waves.

DISCLOSURE OF INVENTION

The present invention has been made to solve the above-mentioned conventional problems, and its object is to provide a highly reliable ultrasonic probe with excellent resistance to an external shock.

In order to achieve the above-mentioned object, an ultrasonic probe according to the present invention includes: an ultrasonic element unit for transmitting and receiving an ultrasonic wave while carrying out ultrasonic scanning; a storage portion for storing the ultrasonic element unit; and an acoustic medium liquid charged in the storage portion, wherein the ultrasonic element unit is supported by an elastic supporting member, and the storage portion is sealed by the supporting member in a liquid-tight state.

DESCRIPTION OF THE INVENTION

As described above, in the ultrasonic probe according to the present invention, the ultrasonic element unit is supported by an elastic supporting member, and the supporting member seals the storage portion for storing the ultrasonic element unit and the acoustic medium liquid in a liquid-tight state.

According to the above ultrasonic probe, the ultrasonic element unit is supported by the elastic supporting member in the storage portion. Therefore, even when an external shock is applied to the probe, the supporting member absorbs the shock so as to relieve stress to be applied to the ultrasonic element unit.

Further, the supporting member also serves as a sealing member for sealing the storage portion in a liquid-tight state with its elasticity. Therefore, with the sealing function of the supporting member, even when an external shock is applied to the probe, it is possible to suppress the entry of air bubbles that occurs when the liquid-tight state in the storage portion is broken.

Preferably, the ultrasonic probe further includes pressurizing means for pressurizing the acoustic medium liquid so as to form a positive pressure in the storage portion. According to this preferable example, the pressure in the storage portion is higher than the external pressure. Therefore, it is possible to suppress the entry of air bubbles through a material constituting the storage portion, such as resin and the like.

Preferably, the ultrasonic probe further includes a reservoir connected with the storage portion so as to allow the acoustic medium liquid to flow between the reservoir and the storage portion. According to this preferable example, the reservoir is capable of absorbing an internal pressure fluctuation in the storage portion that is caused by a volume change of the acoustic medium liquid due to a rise in temperature or the like. As a result, it is possible to keep the internal pressure of the storage portion in a desired range so as to suppress air bubbles from entering the storage portion.

Hereinafter, a preferred embodiment of the present invention will be described with reference to the drawings.

Figure 1:
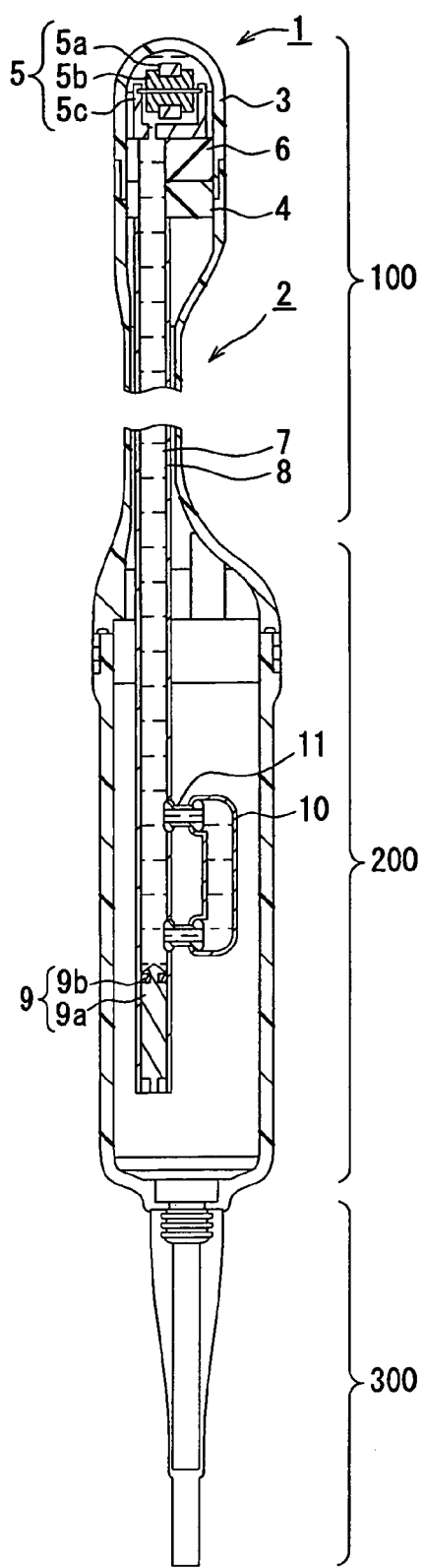
FIG. 1 is a schematic cross-sectional view showing an exemplary structure of an ultrasonic probe according to the present invention.

FIG. 1 is a cross-sectional view showing an exemplary structure of the ultrasonic probe according to the present invention. This ultrasonic probe is an intracorporeal insertion type ultrasonic probe for use in ultrasonic diagnosis. A part of the probe is inserted into a body cavity of a subject, and ultrasonic scanning is carried out in the body cavity. The ultrasonic probe includes an inserting portion 100 to be inserted into the body cavity, and a grip portion 200 held by an operator outside of the body cavity.

Figure 2:
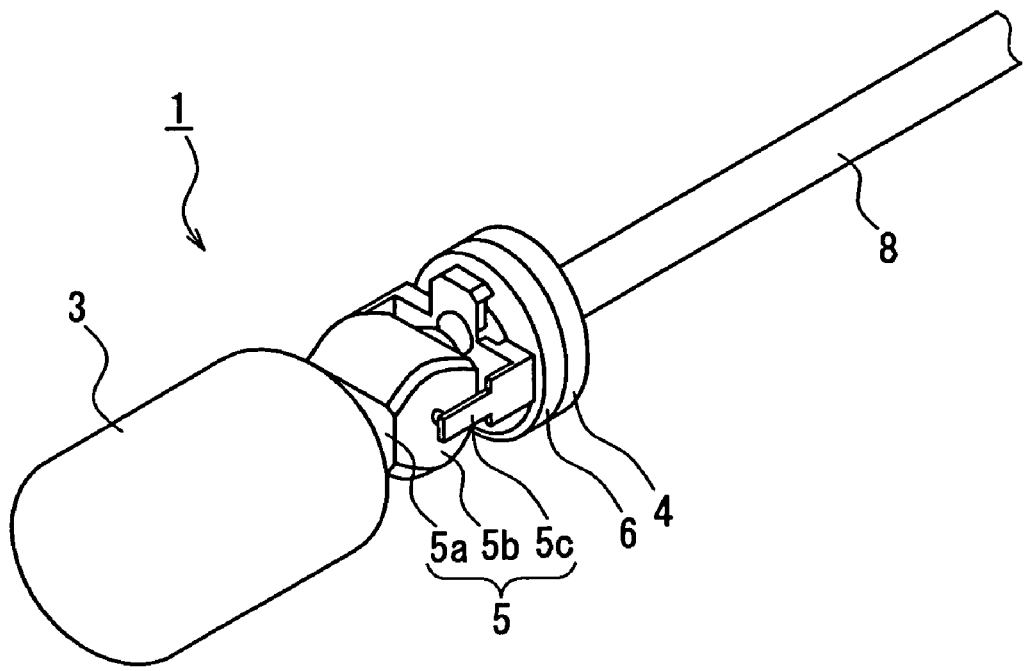
FIG. 2 is a perspective view showing an internal structure of a storage portion of the ultrasonic probe.

The inserting portion 100 includes a storage portion 1 arranged at a front end portion thereof, and a rod portion 2 for locating the storage portion 1 at a desired position in the body cavity. FIG. 2 is a perspective view showing a structure of the storage portion 1. The storage portion 1 is constituted by a window 3 and a frame 4 connected to each other, and stores an ultrasonic element unit 5 therein. Note here that FIG. 2 shows a state where the window is removed from the probe for easy understanding of the internal structure of the storage portion.

The ultrasonic element unit 5 includes an oscillator 5a and a rotating mechanism portion for holding and rotating the same. The rotating mechanism portion, which is a spontaneous rotation type motor whose rotation is induced magnetically, includes a rotor 5b on which the oscillator is mounted, a bracket 5c for rotatably supporting the rotor, and a magnet (not shown) for supplying the rotor with a rotating force. This rotating mechanism portion rotates the oscillator 5a in conjunction with the rotation of the rotor 5b, thereby carrying out mechanical ultrasonic scanning with a circular orbit. Although not shown in the figures, a plurality of signal lines are led out from the ultrasonic element unit 5 so as to transmit and receive an electric signal for driving the oscillator 5a and the rotating mechanism portion. These signal lines are introduced to the grip portion 200 through the rod portion 2.

The storage portion 1 further includes a supporting member 6, on which the bracket 5c of the rotating mechanism portion is fixed. The supporting member 6, which is an elastic member for supporting the rotating mechanism portion, absorbs an external shock applied to the rotating mechanism portion with its elasticity. The supporting member 6 is provided so as to be in close contact with an inner wall of the window 3, thereby sealing the storage portion 1 in a liquid-tight state.

There is no particular limit to the material of the supporting member 6, as long as the elasticity is exhibited. Preferably, rubber may be used. The elasticity of the supporting member 6 is set in a range in which an external shock applied to the rotating mechanism portion can be absorbed and the rotating mechanism portion can be supported. For example, in the case of using rubber, preferably, the hardness thereof is set in a range of 30 to 95 (JIS Spring type, unit: Hs). Further, there is no particular limit to the shape of the supporting member 6. For example, the supporting member 6 may have a shape (e.g., a shape similar to a hat shape) in which a portion on which the rotating mechanism portion is mounted is formed of a hollow convexity, or a shape in which a plurality of concentric grooves are formed on a surface on which the rotating mechanism portion is mounted.

The storage portion 1 is charged with a deaerated acoustic medium liquid 7. Each of the supporting member 6 and the frame 4 has a through hole connected with a pipe extending to the grip portion 200 through the rod portion 2. The pipe 8 also is charged with the acoustic medium liquid 7. With this configuration of the storage portion 1, the acoustic medium liquid 7 is allowed to flow through the pipe 8 between the storage portion 1 and pressurizing means 9 as well as a reservoir 10 to be described later.

Figure 3:
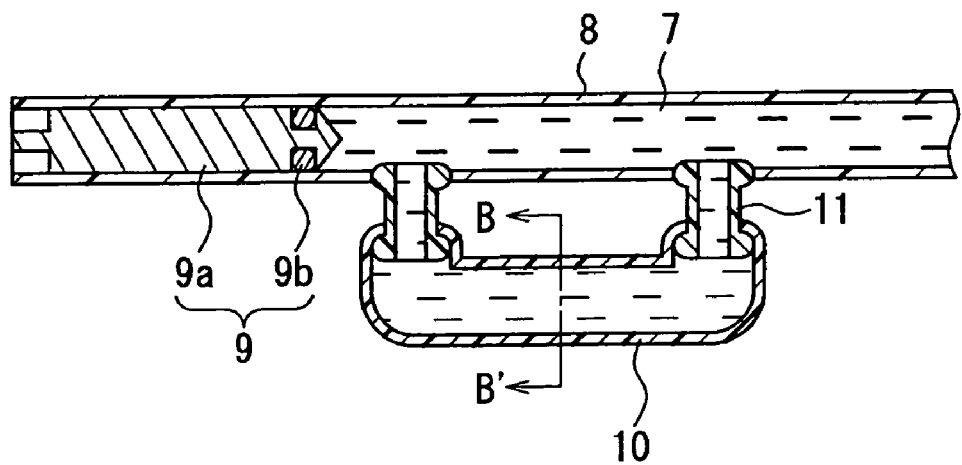
FIG. 3 is a perspective view showing structures of pressurizing means and a reservoir of the ultrasonic probe.

The grip portion 200 includes the pressurizing means 9 and the reservoir 10 for adjusting the internal pressure of the storage portion 1. A cable 300 is led out from the grip portion 200, and the ultrasonic probe is connected with an ultrasonic diagnostic apparatus via the cable 300. FIG. 3 is a cross-sectional view showing structures of the pressurizing means 9 and the reservoir 10.

The pressurizing means 9 pressurizes the acoustic medium liquid 7 so as to form a positive pressure in the storage portion 1. In FIG. 3, the pressurizing means 9 is a syringe pump configured to extrude the acoustic medium liquid 7 into the storage portion 1. This syringe pump includes a cylinder connected with the pipe 8, and a piston 9a arranged in the cylinder. As shown in FIG. 3, a part of the pipe 8 may be used as the cylinder. An O ring 9b is arranged between the cylinder (pipe 8) and the piston 9b so as to ensure liquid-tightness therebetween.

The grip portion 200 further includes the reservoir 10 connected with the pipe 8 via nozzles 11. The reservoir 10 is charged with the acoustic medium liquid 7, and is configured so as to allow the acoustic medium liquid 7 to flow between the reservoir 10 and the storage portion 1 as described above. The reservoir 10 is constituted by an elastic container whose volumetric capacity can be changed in accordance with a charged amount of liquid when the reservoir 10 is charged with the liquid.

Preferably, the change in the volumetric capacity of the reservoir 10 is caused not only due to stretching of its material but also due to deformation of the container. In other words, preferably, the volumetric capacity of the container can be changed without changing the surface area thereof Further, preferably, the change in the volumetric capacity is caused due to deformation of the container in preference to stretching of the material.

Figure 4:
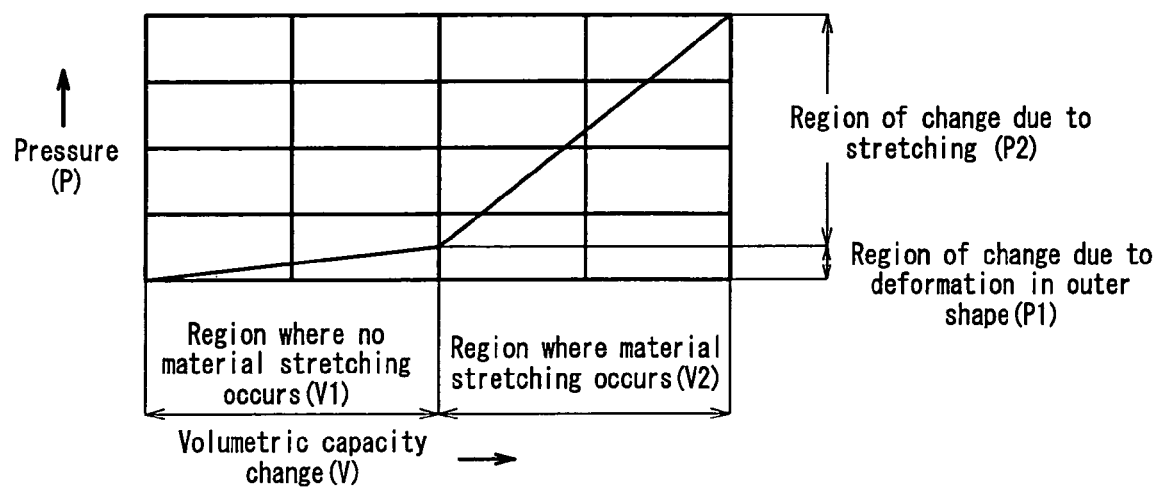
FIG. 4 is a characteristic diagram showing an exemplary relationship between a charged amount of liquid and an internal pressure when the reservoir is charged with a liquid.

FIG. 4 is a characteristic diagram showing an exemplary relationship between a charged amount of liquid and an internal pressure when the above-described preferable reservoir is charged with the liquid. With respect to this reservoir, in a region where the charged amount of liquid is relatively small, the material is not stretched, and the volumetric capacity is changed due to deformation of the container preferentially. In general, the internal pressure required to deform the container is lower than that required to stretch the material. Thus, as shown in the figure, with respect to the reservoir, in the region (V1) where the charged amount of liquid is relatively small, a change in the internal pressure of the reservoir is small. On the other hand, in a region (V2) where the charged amount of liquid becomes larger beyond the limit of the volumetric capacity that is changed due to deformation of the container, the change in the internal pressure of the reservoir becomes greater due to stretching of the material. There is no particular limit to the internal pressure (P) at the limit of the volumetric capacity that is changed due to deformation. For example, this internal pressure may be 800 hPa to 100 hPa, and preferably 500 hPa to 300 hPa. In FIG. 4, the change in characteristics in each of the regions V1 and V2 may be represented by a curve instead of a linear line.

Figure 5A:
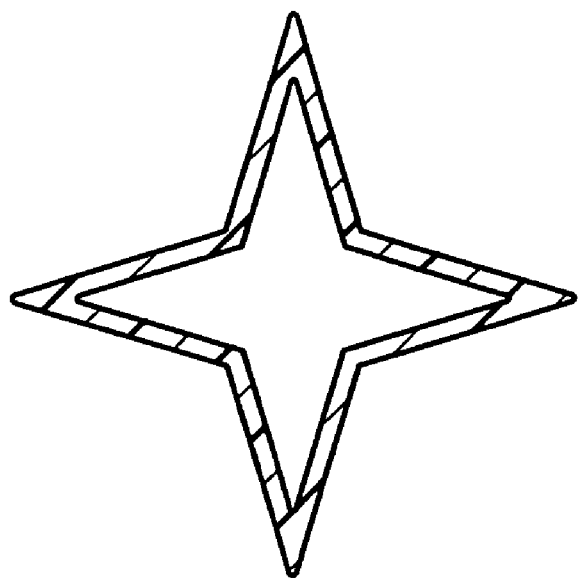
FIGS. 5A and 5B are cross-sectional views showing exemplary shapes of the reservoir of the ultrasonic probe.
Figure 5B:
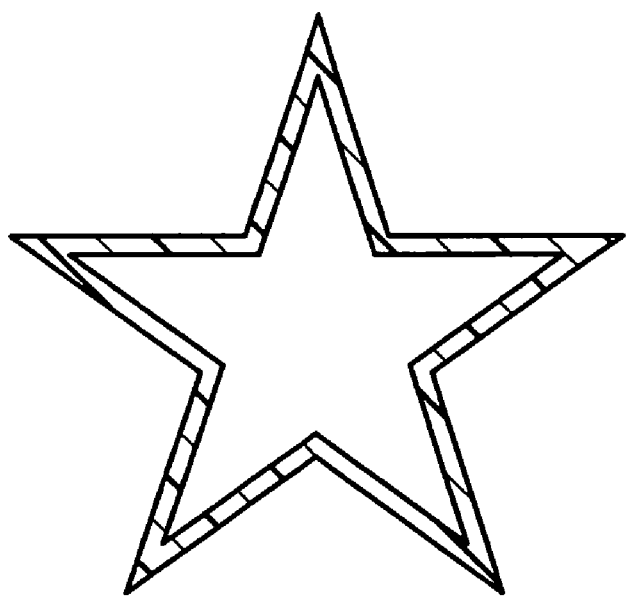

FIGS. 5A and 5B are cross-sectional views showing exemplary shapes of the reservoir 10 having the preferable characteristics as described above, each figure showing a cross section taken along a line B-B' in FIG. 3. As shown in the figures, preferably, the reservoir 10 is constituted by a container with concavities. In particular, preferably, a container with V-shaped groove concavities is used, such as a container having a star-shaped cross section, and the like. Further, preferably, the reservoir 10 is capable of retaining the above-mentioned shape also in a state where no liquid is charged therein, and is not deformed in a state where the liquid flows therein naturally.

There is no particular limit to the container for use as the reservoir 10, as long as the elasticity is exhibited. For example, a resin material such as rubber, polyethylene, polypropylene, and vinyl chloride, or a metal material with a thickness that allows easy deformation may be used.

Next, an operation of the ultrasonic probe will be described.

Initially, the ultrasonic probe is located in the vicinity of a subject, and the rotating mechanism portion is driven so as to rotate the rotor 5b. Accordingly, the oscillator 5a mounted on the rotor 5b is rotated. Then, an electric signal (transmission signal) from the ultrasonic diagnostic apparatus is transmitted to the oscillator 5a. The transmission signal is converted into an ultrasonic wave by the oscillator 5a, and the ultrasonic wave is transmitted through the acoustic medium liquid 7 to the subject from the window 3. The ultrasonic wave is reflected by the subject, and a part of the reflected wave is received, converted into an electric signal (reception signal), and transmitted to the ultrasonic diagnostic apparatus by the oscillator 5a. The reception signal is converted into image data by the ultrasonic diagnostic apparatus.

This operation of transmitting and receiving an ultrasonic wave is performed repeatedly while the rotor 5b is rotated, thereby carrying out ultrasonic scanning. In the ultrasonic probe, since the oscillator 5a is rotated in conjunction with the rotation of the rotor 5b, scanning can be carried out 360 degrees around a rotation axis of the rotor 5b. By carrying out scanning in this manner, a disk-shaped tomographic image in a direction perpendicular to the rotation axis can be obtained. However, in general, the ultrasonic diagnostic apparatus displays a part of the disk-shaped image corresponding to a selected angle as a fan-shaped tomographic image. When a plurality of the same type of oscillators 5a are mounted on the rotor 5b, the scanning speed can be multiplied. When a plurality of different types of oscillators 5a are mounted, a plurality of different tomographic images can be obtained.

In the ultrasonic probe, the ultrasonic element unit 5 is fixed on the elastic supporting member 6. The supporting member 6 absorbs an external shock, so that stress to be applied to the ultrasonic element unit due to the external shock can be relieved. Therefore, it is possible to suppress deformation or a breakage caused by a shock of dropping or the like, thereby increasing the reliability of the probe.

The above description has been given taking as an example the probe using the ultrasonic element unit for carrying out mechanical ultrasonic scanning. However, the present invention is not limited thereto, and the probe may use an ultrasonic element unit with an array element for carrying out electronic scanning.

Next, a function of the pressurizing means will be described.

As described above, the pressurizing means forms a positive pressure in the storage portion. In the case where the window is made of rigid resin, which exhibits slight gas permeability, air bubbles may enter the storage portion after the elapse of a long period of time. However, the use of the pressurizing means makes it possible to form a positive pressure in the storage portion, so that the entry of air bubbles can be suppressed.

In the case of using the pressurizing means constituted by a syringe pump as shown in FIGS. 1 and 3, when charging the storage portion with the acoustic medium liquid during assembly of the probe, it is possible to use an end portion (end portion on a side opposite to that of the storage portion) of the cylinder (pipe 8 in the example in FIG. 1) of the pressurizing means as a liquid inlet. Hereinafter, a description will be given of a procedure for charging the probe in FIGS. 1 and 3 with the acoustic medium liquid by way of example. Initially, in a state where the piston 9a and the O ring 9b are not inserted, a liquid injection tube is connected to the end portion of the pipe 8 so as to inject the acoustic medium liquid 7 therethrough. The liquid injection can be performed in a state where the liquid is allowed to enter the pipe 8 easily, the state being realized by, for example, forming a negative pressure in the pipe 8, raising the temperature in the pipe 8, or the like. When a predetermined amount of liquid is injected, the liquid injection tube is removed from the pipe 8. At this time, the pressure in the storage portion 1 and that in the pipe 8 are kept almost in equilibrium. Thereafter, the piston 9a on which the O ring 9b is mounted is inserted into the pipe 8 from the end portion thereof. The position of the piston 9a in the pipe 8 is adjusted arbitrarily depending upon an amount of the piston 9a pushed into the pipe 8.

When the piston 9a is inserted, the acoustic medium liquid 7 in the pipe 8 is pressurized, so that a positive pressure is formed in the storage portion 1. The internal pressure of the storage portion 1 can be adjusted in accordance with the pushed amount of the piston 9a. For example, by examining beforehand the relationship between the pushed amount and the internal pressure, a desired internal pressure can be obtained with only an easy operation of locating the piston 9a at a predetermined position. The initial pressure of the acoustic medium liquid 7 in the ultrasonic probe is set so as to be positive at a target or set minimum temperature of, for example, 10 degrees below zero.

As described above, the use of the pressurizing means eliminates the need to provide an inlet and a valve mechanism specifically designed to form a positive pressure in the storage portion. As a result, it is possible to simplify the injection mechanism portion for injecting the acoustic coupling medium liquid, arrange the components in a small space, and reduce the component count, resulting in a reduction in the size and cost of the probe on the whole.

Next, a function of the reservoir will be described.

As described above, the reservoir is a container whose volumetric capacity can be changed and that is provided so as to communicate with the storage portion. The use of such a container makes it possible to accommodate a volume change of the acoustic medium liquid caused by a temperature change and to suppress an internal pressure fluctuation in the storage portion. More specifically, when the acoustic medium liquid is contracted, and the internal pressure of the storage portion is reduced, the volumetric capacity of the reservoir is reduced, so that the acoustic medium liquid is supplied from the reservoir to the storage portion, thereby increasing the internal pressure of the storage portion. On the other hand, when the acoustic medium liquid is expanded, and the internal pressure of the storage portion is increased, the volumetric capacity of the reservoir is increased, thereby reducing the internal pressure of the storage portion.

In particular, when the reservoir is constituted by a container (e.g., a container exhibiting the characteristics as shown in FIG. 4) whose volumetric capacity is changed due to deformation of the container in preference to stretching of its material as described above, the pressure fluctuation in the storage portion can be suppressed further. This will be described hereinafter by taking as an example the probe (i.e., the probe including the pressurizing means) shown in FIGS. 1 and 3 that is provided with the reservoir exhibiting the characteristics as shown in FIG. 4.

During the above-mentioned procedure for charging the acoustic medium liquid 7, the pressure in the storage portion 1 and the external pressure are kept in equilibrium after the storage portion 1 is charged with the acoustic medium liquid 7 and before the acoustic medium liquid 7 is pressurized by the pressurizing means 9. At this time, the reservoir 10 retains its initial shape when it is mounted, and the internal pressure thereof is almost equal to the external pressure. Then, when the acoustic medium liquid 7 is pressurized by the pressurizing means 9, the acoustic medium liquid 7 further flows into the reservoir 10, where it is pressurized. At this time, the reservoir 10 still is subjected only to deformation with no stretching of the material itself caused. This state is represented by a V1-P1 region in FIG. 4.

In this state, when the liquid is expanded due to a rise in temperature, the expanded liquid increases the volumetric capacity of the reservoir 10. This change in the volumetric capacity is not due to stretching of the material but due to deformation. As shown by the V1-P1 region in FIG. 4, although a slight increase in pressure is caused, it is obviously smaller than that caused by the change in the volumetric capacity due to stretching of the material. Accordingly, the change in the internal pressure of the storage portion can be suppressed within a relatively small range, resulting in a small influence exerted on the performance of the probe. On the other hand, when the liquid is contracted due to a decrease in temperature, the volumetric capacity of the reservoir 10 is reduced. Also in this case, as shown by the V1-P1 region in FIG. 4, although a slight decrease in pressure is caused, it is small similarly, and thus degradation in performance of the probe is suppressed.

INDUSTRIAL APPLICABILITY

The ultrasonic probe according to the present invention can be applied effectively to ultrasonic diagnostic apparatuses to be utilized in various medical fields.

The invention claimed is:

1. An ultrasonic probe, comprising:
an ultrasonic element unit for transmitting and receiving an ultrasonic wave while carrying out ultrasonic scanning;
a storage portion for storing the ultrasonic element unit;
an acoustic medium liquid charged in the storage portion; and
pressurizing means for presurrizing the acoustic medium liquid so as to form a positive pressure in the storage portion,
wherein the ultrasonic element unit includes a rotating mechanism portion stored in the storage portion, the rotating mechanism portion being a spontaneous rotation type motor whose rotation is induced magnetically and being supported by an elastic supporting member, and
the storage portion is sealed by the supporting member in a liquid-tight state.

2. The ultrasonic probe according to claim 1, wherein the pressurizing means is a syringe pump including a cylinder connected with the storage portion so as to allow the acoustic medium liquid to flow between the cylinder and the storage portion, and a piston arranged in the cylinder.

3. The ultrasonic probe according to claim 2, wherein the cylinder is sealed by the piston in a liquid-tight state.

* * * * *